United States Patent [19]

Karickhoff

[11] 4,319,564
[45] Mar. 16, 1982

[54] INSTRUMENT FOR MEASUREMENT OF THE DIAMETER OF THE ANTERIOR CHAMBER OF THE EYE

[76] Inventor: John R. Karickhoff, 8615 Crestview Dr., Fairfax, Va. 22046

[21] Appl. No.: 109,318

[22] Filed: Jan. 3, 1980

[51] Int. Cl.³ .............................................. A61B 5/00
[52] U.S. Cl. .................................. 128/774; 33/174 D
[58] Field of Search ...................... 128/774, 303; 3/13; 33/143 C, 143 M, 143 K, 174 D

[56] References Cited

U.S. PATENT DOCUMENTS

| 1,598,248 | 8/1926 | Paine | 33/143 M X |
| 2,122,068 | 6/1938 | Meyers | 33/143 C X |
| 2,677,894 | 5/1954 | Belgard | 33/143 M X |
| 2,700,825 | 2/1955 | Sorensen | 33/143 M |
| 3,213,541 | 10/1965 | Raffman | 128/774 X |
| 3,315,369 | 4/1967 | Johnson | 33/143 M X |
| 3,430,346 | 3/1969 | Dritz | 33/143 M X |
| 4,177,571 | 12/1979 | Renier | 33/174 D X |

FOREIGN PATENT DOCUMENTS 807234 6/1951 Fed. Rep. of Germany ... 33/174 D

Primary Examiner—Robert W. Michell
Assistant Examiner—Francis J. Jaworski
Attorney, Agent, or Firm—Robert H. Epstein

[57] ABSTRACT

An instrument for measurement of the diameter of the anterior chamber of the eye includes an elongate member for insertion into the anterior chamber through an incision in the cornea having a flared distal end for positioning against the juncture of the iris and the cornea opposite the incision, a slide movable along the elongate member having an arm depending therefrom and extending away from the distal end of the elongate member to terminate in a flared end for positioning against the juncture of the iris and the cornea adjacent the incision, and indicia means including a scale and a pointer carried on the elongate member and the slide such that movement of the slide to position the flared end of the arm against the juncture of the iris and the cornea adjacent the incision causes relative movement of the scale and the pointer to provide an indication of the diameter of the anterior chamber.

12 Claims, 5 Drawing Figures

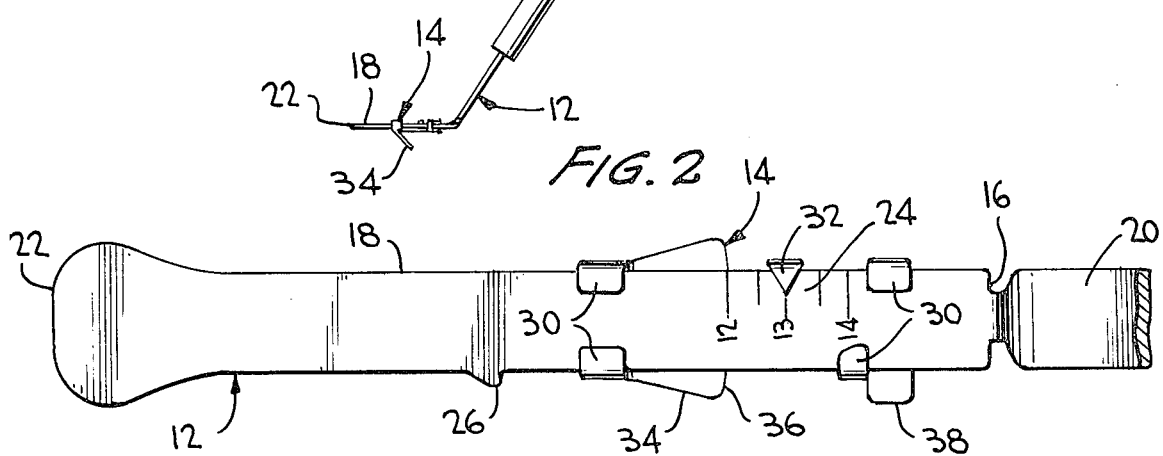
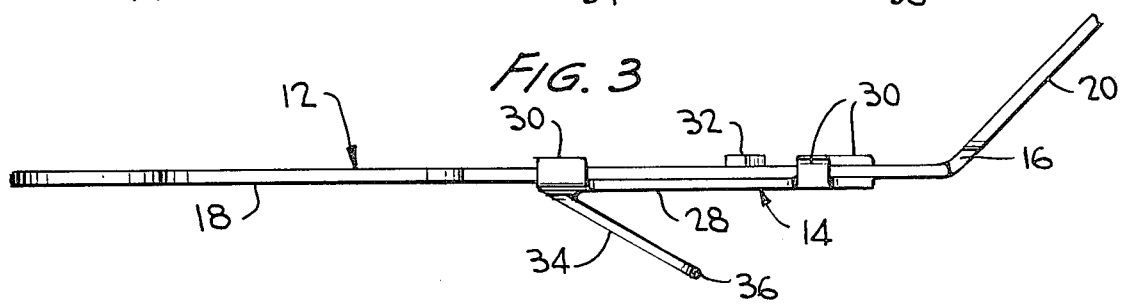
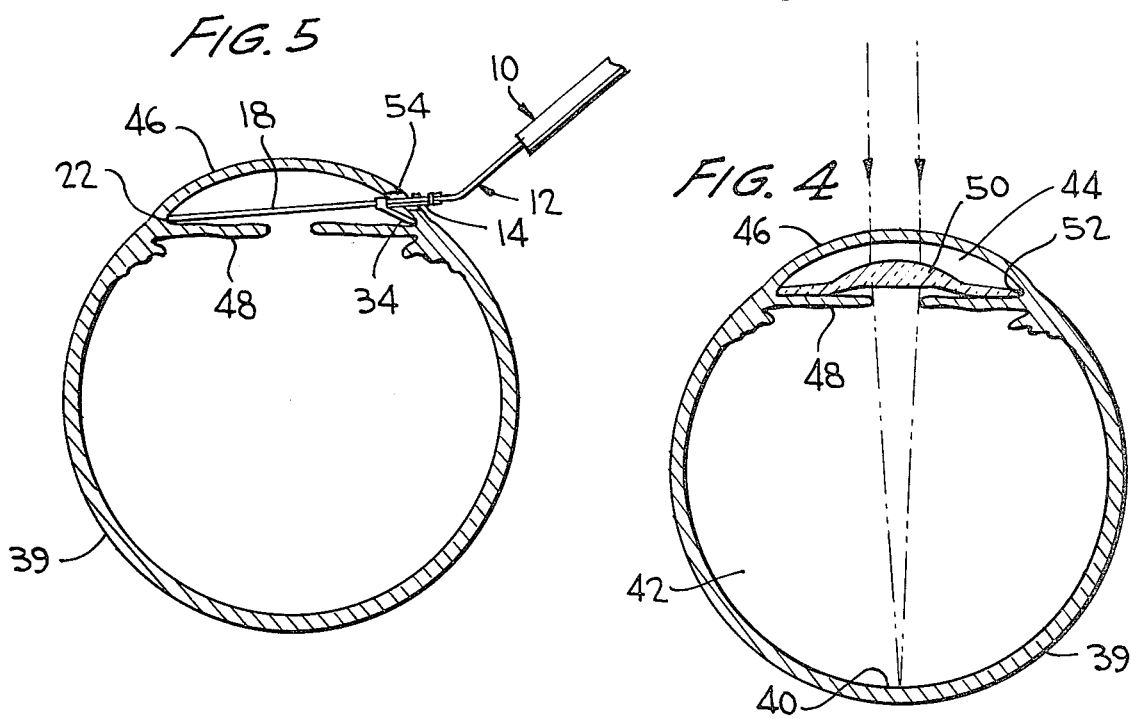

INSTRUMENT FOR MEASUREMENT OF THE DIAMETER OF THE ANTERIOR CHAMBER OF THE EYE

BACKGROUND OF THE INVENTION

1. Field of the Invention

The present invention pertains to measurement of the diameter of the anterior chamber of the eye and, more particularly, to an instrument for use in such measurement to facilitate selection of an intraocular lens of correct dimensions for insertion in the anterior chamber.

2. Discussion of the Prior Art

Surgical operations to remove cataracts of the eye require removal of the lens thereby permitting the patient to see only vague forms since light will not be focused on the retina at the back of the eye. Accordingly, following cataract eye surgery, some means must be provided to focus light for the patient to have clear vision. For example, cataract glasses can be placed in front of the eye, a contact lens can be placed on the eye, or an artificial intraocular lens can be positioned inside the eye to restore vision. Cataract glasses are effected in restoring straight ahead vision, but have the disadvantage of permitting only limited peripheral vision. Contact lenses are effective in restoring straight ahead and peripheral vision; however, elderly patients, who represent a great majority of those undergoing cataract surgery, have great difficulty inserting and removing the contact lenses on a daily basis. Intraocular lenses provide the most normal visual correction of the above-mentioned means for focusing light in that they restore straight ahead and peripheral vision, do not change the size of objects viewed significantly, and are permanently implanted.

There are essentially three types of intraocular lenses categorized according to their position inside the eye. Posterior lenses are placed behind the iris, while iris supported lenses are clipped, hooked or sewed onto the iris, and anterior chamber lenses are positioned in the anterior chamber of the eye bounded by the corneal dome and the iris plane. Anterior chamber lenses are supported in the anterior chamber by feet positioned at the juncture of the iris with the cornea.

While one size of iris supported or posterior lenses essentially can be utilized for all human eyes since the supports therefor do not abut rigid structures of the eye, the support feet of anterior chamber lenses are placed directly against the sclera; and, thus, anterior chamber lenses must fit the recipient eye exactly. For this reason, manufacturers of anterior chamber lenses typically supply such lenses in 12.0, 12.5, 13.0, 13.5, and 14.0 millimeter sizes, and all of these sizes must be stocked in the operating room so that the correct size implant lens can be used for the recipient eye once the cataracts are removed. If the implant lens is too short for the recipient eye, it can ride forward causing blistering of the cornea, can rotate causing continual inflammation of the eye and can, on rare occasions, cause hemorrhaging. If the implant is too long for the recipient eye, it can cause large amounts of of astigmatism, tenderness to touch and continual inflammation as well as increasing the chances of producing hemorrhage as the implant lens is inserted into the eye. If the wrong size anterior chamber implant lens is inserted into the eye and this is recognized at the time of surgery, the surgeon must remove the lens and insert another implant lens. This exchange is made after the cataract has been removed and when the vitreous is exposed to the air. In this situation, there is danger of the vitreous being lost from the eye. This is a serious complication in cataract surgery. Thus the need to place the correct size implant in the eye on the first attempt. While anterior chamber implant lenses are widely accepted, they pose the additional challenge to the surgeon of correct sizing since the anterior chamber typically varies in diameter from 12.0 to 14.5 millimeters.

The most widely used method of estimating the diameter of the anterior chamber is to measure the horizontal, clear corneal diameter externally of the eye and add 1 millimeter to such measurement under the assumption that the internal anterior chamber diameter is 1 millimeter larger than the external cornea measurement; however, in clinical investigations, it has been determined that the actual implant lens size required was the same as that predicted by this method in only 65% of the cases. In fact, it has been found that the difference between the external and internal measurements do not average 1 millimeter as this method assumes but, rather, the average difference is on the order of 0.6 millimeters and varies greatly from eye to eye, the smallest difference being 0.3 millimeters and the largest difference being 1.2 millimeters.

Another method of estimating the anterior chamber diameter utilizes a ruler-type instrument that is passed through a surgical incision across the anterior chamber until the distal end abuts the juncture of the cornea and the iris, the ruler having a scale in the pupil area such that the surgeon estimates the position of the center of the cornea, and this distance is doubled to obtain an estimate of the diameter of the anterior chamber. This instrument has the disadvantages that it is an indirect method of measurement since only one side of the anterior chamber is contacted and the scale can be difficult to read if there are any air bubbles or blood in the anterior chamber. An improvement over this instrument utilizes a ruler-type instrument passed through the surgical incision across the anterior chamber until its distal end touches the juncture of the iris and the cornea with the measuring scale of the ruler lying at the surgical incision such that the scale is easier to read. This instrument has the disadvantage that it remains an indirect method of determining anterior chamber diameter because the instrument touches on only one side of the anterior chamber and the surgeon must estimate the location of the juncture of the iris and cornea below the incision since it cannot be seen, the location of this juncture varying somewhat with the location of the incision.

Attempts have been made to utilize ultrasonic techniques for measuring the diameter of the anterior chamber of the eye; however, such attempts have had the disadvantages of involving a complicated hand-held method of simultaneously performing an A-scan and a B-scan and, thus, being quite time consuming and requiring much practice.

SUMMARY OF THE INVENTION

Accordingly, it is a primary object of the present invention to overcome the above-mentioned disadvantages of the prior art by providing an instrument for direct measurement of the diameter of the anterior chamber of the eye to permit accurate selection of an artificial, intraocular anterior chamber implant lens of the correct size for insertion in the anterior chamber.

Another object of the present invention is to utilize a slide mounted on an elongate member for insertion into the anterior chamber of the eye, the slide having an arm depending therefrom and extending away from the distal end of the elongate member such that the end of the arm can be positioned against the juncture of the iris and the cornea adjacent the incision, and relative indicia means carried by the elongate member and the slide can be seen by the surgeon to determine directly the diameter of the anterior chamber.

A further object of the present invention is to provide a measuring scale on an elongate member for insertion in the anterior chamber of the eye, the scale being positioned so as to be external of the eye when the elongate member is inserted in the anterior chamber, and a slide movable along the elongate member carrying a pointer such that the pointer is movable over the scale to provide a direct measurement of the anterior chamber diameter of the eye while being external of the eye and easily visible.

An additional object of the present invention is to measure the diameter of the anterior chamber of the eye with an instrument contacting the junctures of the iris and cornea at diametrically opposed positions to obviate the necessity of approximations or estimates.

Some of the advantages of the present invention over the prior art are that the instrument for measurement of the diameter of the anterior chamber of the eye according to the present invention provides direct measurement thereof to permit precise selection of size of anterior chamber intraocular implant lenses, the instrument can be easily used and manipulated by a surgeon, the instrument is simple in construction to facilitate manufacture and surgical use, and the instrument can be manufactured to be autoclavable or disposable.

The present invention is generally characterized in an instrument for measurement of the diameter of the anterior chamber of the eye including an elongate member adapted to be inserted into the anterior chamber through an incision in the cornea adjacent but spaced from the iris, the elongate member having a distal end adapted to be positioned against the juncture of the iris and the cornea opposite the incision, a slide mounted on the elongate member for movement therealong having a body engaging the elongate member and an arm depending therefrom and extending away from the distal end of the elongate member along the body of the slide, first indicia carried on the slide, and second indicia carried on the elongate member whereby movement of the slide to position the end of the arm of the slide against the juncture of the iris and the cornea adjacent the incision causes relative movement of the first and second indicia to indicate the diameter of the anterior chamber.

Other objects and advantages of the present invention will become apparent from the following description of the preferred embodiment taken in conjunction with the accompanying drawings.

BRIEF DESCRIPTION OF THE DRAWINGS

FIG. 1 is a side view of an instrument for measurement of the diameter of the anterior chamber of the eye in accordance with the present invention.

FIG. 2 is a top plan view of the measuring portion of the instrument of FIG. 1.

FIG. 3 is a side elevation of the measuring portion of the instrument of FIG. 1.

FIG. 4 is a cross section of an eye having an anterior chamber intraocular implant lens therein.

FIG. 5 is a cross section of an eye with the instrument of the present invention inserted therein for measurement of the anterior chamber.

DESCRIPTION OF THE PREFERRED EMBODIMENT

An instrument 10 for measurement of the diameter of the anterior chamber of an eye in accordance with the present invention is illustrated in FIGS. 1, 2 and 3 and includes, as basic components, an elongate member 12 and a slide 14 movable along the elongate member. The elongate member 12 is bent to define a measuring portion 18 and a handle portion 20, and the elongate member has cut out grooves or recesses 16 disposed in opposite edges at the junction of the measuring and handle portions to permit the slide 14 to be mounted on the elongate member. The measuring portion 18 is rectangular in cross section and has a thickness on the order of 0.25 mm and a width on the order of 2.0 mm. The distal end 22 of the measuring portion 18 defines a contact edge and is flared to have a width of approximately 3.0 mm with curved edges, and measuring scale indicia 24 is carried on the top surface of a proximal portion of the measuring portion of the elongate member, the scale indicia ranging from 12 mm to 14 mm. The length of the measuring portion is preferably about 17 mm with the scale indicia 24 positioned a distance from the distal end 22 in accordance with the configuration of the slide such that the scale indicia is positioned externally of the eye when the measuring portion is fully inserted in the anterior chamber. A stop 26 protrudes from the side of the measuring portion 18 to limit movement of the slide 14 toward the distal end 22. The handle portion 20 of the elongate member 12 has an increased cross sectional configuration to facilitate gripping for manipulation of the instrument 10 by a surgeon.

The slide 14 has a body 28 extending along the underside of the measuring portion 18 with spaced prongs 30 extending from the body and bent around the measuring portion to mount the slide thereon. Indicia in the form of a pointer 32 extends from the body over the scale indicia 24, and an arm 34 depends from the body 28 and extends along the body away from the distal end 22 of the measuring portion to terminate at a flared end 36 defining a contact edge having a width substantially the same as the width of the distal end 22 a flattened dimension of the arm defining a plane including the contact edge extending at an acute angle from the proximal portion of the measuring portion of the elongate member. A protrusion 38 extends transversely from body 28 to facilitate movement of the slide along the elongate member by a surgeon. The slide has a length of approximately 6 mm and is made of material having a thickness on the order of 0.25 mm.

The elongate member 12 and slide 14 can be made from stainless steel to render the instrument 10 autoclavable for repeated use. The elongate member can be stamped out of one piece of stainless steel and tooled to proper dimensions, and the slide can be stamped out of another piece of stainless steel of the same thickness with flaps extending from the body to be bent to form prongs 30, pointer 32, arm 34 and protrusion 38 with the edges of the elongate member and the slide finely polished and rounded. The instrument 10 can also be constructed inexpensively to be economically disposable by injection molding of the elongate member 12 and the slide 14 of a high quality plastic or similar material.

A cross section of an eye 39 is illustrated in FIG. 4 with the retina 40 disposed at the back of the vitreous cavity 42 and the anterior chamber 44 bounded by the cornea 46 and the iris 48, the lens having been removed by a surgical procedure. An anterior chamber intraocular lens 50 is disposed in the anterior chamber 44 and has feet engaging the juncture 52 of the cornea and the iris to properly position the lens 50 to focus light on the retina 40.

The diameter of the anterior chamber can be measured with the instrument 10 of the present invention by forming an incision 54 in the cornea adjacent but spaced from the iris 48, as illustrated in FIG. 5, and inserting the elongate member 12 through the incision such that the distal end 22 of the measuring portion 18 of the elongate member is positioned against the juncture of the iris and the cornea opposite the incision, the slide 14 also being inserted through the incision into the anterior chamber. An air bubble is formed in the anterior chamber after the incision is widened to about 160° to prevent the instrument 10 from touching the backside of the cornea. The protrusion 38 extending from the slide is grasped by the surgeon with the use of an instrument, such as a forceps, and the slide is gently moved along the measuring portion of the elongate member until the end 36 of the arm 34 touches the juncture of the iris and cornea adjacent the incision. The diameter of the anterior chamber can now be read directly from the position of the pointer 32 on the scale 24. The slide is now moved toward the distal end of the elongate member slightly and the arm is elevated such that the entire instrument 10 can be removed from the eye. The measurement is preferably made while the lens is still in the eye thereby preventing any possible loss of vitreous. Once the instrument is removed, the lens can be surgically removed and an anterior chamber intraocular lens implant of a precise size required by the recipient eye can be inserted in the anterior chamber via the incision.

The stop 26 is positioned along the measuring portion 18 at a location to abut the prongs 30 of the slide to limit movement thereof towards the distal end to only a desired amount. While the indicia 24 and 32 are illustrated as being arranged such that the scale is carried by the elongate member and the pointer is carried by the slide, it should be recognized that the scale indicia could be carried on the slide and the pointer carried on the elongate member to provide a similar relative measuring operation.

Inasmuch as the present invention is subject to many variations, modifications and changes in detail, it is intended that all subject matter discussed above or shown in the accompanying drawings be interpreted as illustrative and not in a limiting sense.

What is claimed is:

1. An instrument for measurement of the diameter of the anterior chamber of the human eye comprising
   an elongate member of a size so as to be adapted to be inserted into the anterior chamber of a human eye through an incision in the cornea adjacent but spaced from the iris, said elongate member having a proximal portion and a distal end having a contact edge adapted to be positioned against the juncture of the iris and the cornea opposite the incision;
   a slide mounted on said elongate member for movement therealong having a body engaging said elongate member and an arm depending therefrom and extending away from said distal end of said elongate member along said body of said slide to a contact edge, said arm having a flattened dimension defining a plane including said contact edge, said plane extending at an acute angle with said proximal portion of said elongate member;
   first indicia means carried on said slide; and
   second indicia means carried on said proximal portion of said elongate member whereby movement of said slide to position the end of said arm of said slide against the juncture of the iris and the cornea adjacent the incision causes relative movement of said first and second indicia means to indicate the diameter of the anterior chamber.

2. An instrument as recited in claim 1 wherein said second indicia means includes measuring scale indicia and said first indicia means includes a pointer movable along said measuring scale indicia.

3. An instrument as recited in claim 2 wherein said elongate member includes a measuring portion adapted to be inserted into the anterior chamber and carrying said measuring scale indicia and a handle portion extending angularly from said measuring portion to be gripped during measurement.

4. An instrument as recited in claim 3 wherein said distal end of said elongate member is wider than said elongate member and the end of said arm of said slide has a width substantially the same as said width of said distal end of said elongate member.

5. An instrument as recited in claim 4 wherein said elongate member has cut outs at the junction of said measuring and handle portions to permit mounting of said slide on said elongate member.

6. An instrument as recited in claim 5 wherein said measuring portion of said elongate member has a stop protruding therefrom to limit movement of said slide toward said distal end.

7. An instrument as recited in claim 6 wherein said slide has a protrusion extending therefrom to facilitate movement of said slide along said elongate member.

8. An instrument as recited in claim 7 wherein said elongate member and said slide member are made of metal to be autoclavable.

9. An instrument as recited in claim 1 wherein said elongate member has a stop protruding therefrom to limit movement of said slide toward said distal end.

10. An instrument as recited in claim 1 wherein said slide has a protrusion extending therefrom to facilitate movement of said slide along said elongate member.

11. An instrument as recited in claim 1 wherein said slide has spaced tabs bent to mount said slide on said elongate member.

12. An instrument as recited in claim 2 wherein said measuring scale indicia is disposed on said elongate member a distance from said distal end greater than indicated by said measuring scale indicia whereby said measuring scale indicia is external of the anterior chamber during measurement.

* * * * *